United States Patent [19]

Tabak

[11] Patent Number: 4,658,073
[45] Date of Patent: Apr. 14, 1987

[54] CONTROL SYSTEM FOR MULTISTAGE CHEMICAL UPGRADING

[75] Inventor: Samuel A. Tabak, Wenonah, N.J.

[73] Assignee: Mobil Oil Corporation, New York, N.Y.

[21] Appl. No.: 884,844

[22] Filed: Jul. 11, 1986

Related U.S. Application Data

[63] Continuation-in-part of Ser. No. 779,373, Sep. 23, 1985.

[51] Int. Cl.$^4$ .............................................. C07C 2/00
[52] U.S. Cl. .............................. 585/314; 208/DIG. 1; 364/500; 585/331; 585/332; 585/401; 585/501; 585/701; 585/709; 585/956
[58] Field of Search ............... 585/314, 331, 332, 709, 585/733, 415, 533, 723, 401, 501, 701, 956; 208/DIG. 1; 364/500

[56] References Cited

U.S. PATENT DOCUMENTS

| | | | |
|---|---|---|---|
| 3,969,078 | 7/1976 | Zabransky | 585/701 |
| 3,972,957 | 8/1976 | Zabranksy | 585/701 |
| 4,048,250 | 9/1977 | Garwood et al. | 585/314 |
| 4,139,573 | 2/1979 | Carson | 585/701 |
| 4,150,062 | 4/1979 | Garwood et al. | 585/415 |
| 4,211,885 | 7/1980 | Banks | 585/316 |
| 4,262,155 | 4/1981 | Hutson, Jr. | 585/329 |
| 4,423,274 | 12/1983 | Daviduk et al. | 585/640 |
| 4,450,311 | 5/1984 | Wright et al. | 585/413 |
| 4,482,772 | 11/1984 | Tabak | 585/254 |
| 4,482,969 | 11/1984 | Funk et al. | 585/701 |
| 4,497,968 | 2/1985 | Wright et al. | 585/304 |
| 4,506,106 | 3/1985 | Hsia et al. | 585/312 |
| 4,543,435 | 9/1985 | Gould et al. | 585/330 |
| 4,544,788 | 10/1985 | Daviduk et al. | 585/501 |
| 4,547,602 | 10/1985 | Tabak | 585/314 |

OTHER PUBLICATIONS

"New Synthetic Fuel Routes for Production of Gasoline and Distillate", S. A. Tabak and C. J. Weiss, paper presented at Synfuels, 4th Worldwide Symposium, Nov. 7–9, 1984.
Hydrocarbon Processing, Feb. 1986, pp. 53, 55.

Primary Examiner—Asok Pal
Attorney, Agent, or Firm—Alexander J. McKillop; Michael G. Gilman; L. G. Wise

[57] ABSTRACT

A process control technique for upgrading $C_3$–$C_4$ hydrocarbon feed containing olefins to produce heavier liquid hydrocarbons comprising converting a major portion of $C_3$–$C_4$ olefins in an oligomerization zone by contacting a shape selective medium pore zeolite catalyst at elevated temperature and pressure to make distillate and olefinic gasoline. The oligomerization stage effluent is fractionated to provide distillate and gasoline product and a $C_3$–$C_4$ intermediate stream containing isobutane and unconverted propene and butylene. The $C_3$–$C_4$ intermediate stream is combined under control with a portion of $C_3$–$C_4$ feed and further converting the combined streams in an alkylation zone to make heavier paraffinic hydrocarbons. The olefin feed may be produced by catalytically converting methanol or similar oxygenated hydrocarbons in a known process. Controlled material balance is achieved by accumulating liquid olefin feed to the oligomerization and akylation units using a surge drum with liquid level control. Byproduct isobutane is recovered and recycled under liquid level control operatively connected to determine feed of liquid olefin to the conversion units.

1 Claim, 5 Drawing Figures

CONTROL SYSTEM FOR MULTISTAGE CHEMICAL UPGRADING

This application is a continuation in part of U.S. Pat. application Ser. No. 779,373, filed 23 Sept. 1985, incorporated herein by reference.

BACKGROUND OF THE INVENTION

This invention relates to a control technique developed for an integrated system for converting oxygenates, such as methanol or dimethyl ether (DME), to liquid hydrocarbons. In particular it provides methods and apparatus employed in continuous processes for producing hydrocarbon fuel products or the like by oligomerizing olefins and alkylating isobutane or other isoparaffins with olefins to produce a balanced slate of fuels.

In order to provide an adequate supply of liquid hydrocarbons for use as synfuels or chemical feedstocks, various processes have been developed for converting coal and natural gas to gasoline and distillate. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for making diesel fuel by a multi-stage technique.

Recent developments in zeolite catalysts and hydrocarbon conversion processes have created interest in utilizing olefinic feedstocks, for producing $C_5^+$ gasoline, diesel fuel, etc. In addition to the basic work derived from ZSM-5 type zeolite catalysts, a number of discoveries have contributed to the development of new industrial processes.

The medium pore ZSM-5 type catalysts are useful for converting methanol and other lower aliphatic alcoohols or corresponding ethers to lower olefins and also for oligomerizing olefins. Particular interest has been directed to a catalytic process for converting low cost methanol to valuable hydrocarbons rich in ethene and $C_3^+$ alkenes. Various processes are described in U.S. Pat. Nos. 3,894,107 (Butter et al), 3,928,483 (Chang et al), 4,025,571 (Lago), 4,423,274 (Daviduk et al), 4,433,189 (Young), and 4,543,435 (Gould and Tabak), incorporated herein by reference. It is generally known that the MTO process can be optimized to produce a major fraction of $C_2$-$C_5$ olefins. Prior process proposals have included a separation section to recover ethene and other gases from by-product water and $C_5^+$ hydrocarbon liquids.

SUMMARY OF THE INVENTION

A continuous catalytic process and control techniques thereforhave been developed for for converting olefinic feedstock comprising lower olefins to heavier liquid hydrocarbon product. This invention includes methods and apparatus for converting olefinic feedstock to obtain a gaseous stream rich in ethylene and a first liquid olefinic stream comprising $C_3$-$C_4$ olefin and passing the $C_3$-$C_4$ liquid olefinic stream to a first accumulator vessel. A further reactor stage provides for contacting a major stream portion of the $C_3$-$C_4$ olefins from the accumulator vessel with shape selective medium pore zeolite oligomerization catalyst in a distillate mode catalytic reactor zone at elevated temperature and pressure to provide a heavier hydrocarbon effluent stream comprising distillate, gasoline and lighter hydrocarbons; fractionating the effluent stream to recover distillate, gasoline and a second $C_3$-$C_4$ hydrocarbon stream containing isobutane. A controlled reactor subsystem is provided for further reacting a stoichiometric excess of isobutane from the second $C_3$-$C_4$ hydrocarbon stream with a minor stream of $C_3$-$C_4$ olefin from the first accumulator vessel in an alkylation reactor zone in the presence of acid alkylation catalyst to produce an effluent stream containing $C_7+$ alkylate, fractionating the alkylate reactor effluent stream to recover $C_7+$ alkylate product, a $C_6^-$ light hydrocarbon stream, a stream rich in normal butane and a stream rich in unreacted isobutane, passing unreacted isobutane to a second accumulator vessel; recycling isobutane to the alkylation reactor zone at a predetermined rate; sensing $C_3$-$C_4$ liquid level in the first accumulator vessel; generating a first control signal representative of said first liquid level; adjusting fluid flow control means in response to the first control signal to increase flow rate for the major $C_3$-$C_4$ olefinic liquid stream from the first accumulator to the distillate mode oligomerization reactor zone with increased liquid level in the first accumulator vessel, sensing isobutane liquid level in the second accumulator vessel, generating a second control signal representative of said isobutane liquid level, and increasing flow of the minor $C_3$-$C_4$ olefin stream from the first accumulator to the alkylation reaction zone in response to the second control signal indicating increased isobutane liquid level in the second accumulator.

In a preferred embodiment a control system is provided for achieving material balance in a continuous multistage chemical feedstock conversion process comprising, in combination, (a) a first catalytic conversion stage for producing an intermediate reactant stream from a major liquid feedstream;

(b) means for fractionating first stage effluent to recover a primary reaction product and a liquid by-product stream;

(c) a second catalytic stage for reacting a minor feedstream with the liquid by-product stream for the first stage to yield a secondary product, said liquid by-product stream being combined with a stoichiometric excess of the minor feedstream;

(d) first accumulator means for receiving and holding the feedstock, having flow-controlled liquid outlet means for the major and minor liquid feedstreams, (e) second accumulator means for receiving and holding by-product liquid for recycle to the second catalytic stage for further reaction;

(f) control means for measuring and controlling said major and minor feedstreams, having operatively associated therewith a primary accumulator level sensing and control means for regulating flow to the first conversion stage, and secondary accumulator level sensing and control means for regulating the minor feedstream flow to the second catalytic stage in response to increased accumulation of the by-product liquid.

Other objects and features of the invention will be seen in the following description and drawings.

DESCRIPTION OF THE PREFERRED EMBODIMENTS

Figure 1:
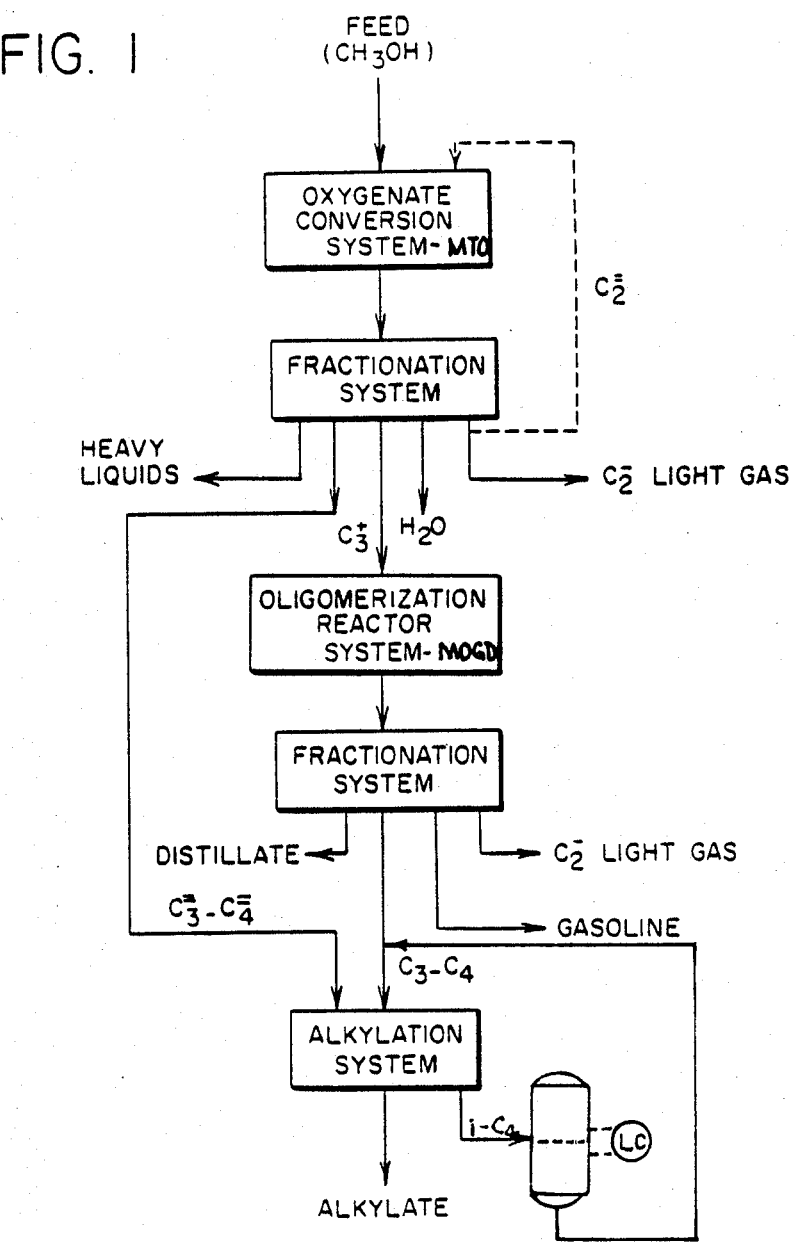
FIG. 1 is a process flow sheet showing the major unit operations and process streams.

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($CH_3OH + CH_3OCH_3 + H_2O$) is produced by partial dehydration. This reaction takes place in either conversion of methanol to lower olefins (MTO) or methanol to gasoline (MTG).

The zeolite catalysts preferred for use herein include the crystalline aluminosilicate zeolites having a silica to alumina ratio of at least 12, a constraint index of about 1 to 12 and acid cracking activity (alpha) of about 1-200. Lower acid zeolites (alpha =1–50) are preferred for the MTO conversion and higher activity (alpha =50–200) is preferred for oligomerization. Representative of the ZSM-5 type zeolites are ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for oxygenate conversion is HZSM-5 zeolite with alumina binder. These medium pore shape selective catalysts are sometimes known as porotectosilicates or 'pentasil' catalysts.

Other catalysts and processes suitable for converting methanol/DME to lower olefins are disclosed in U.S. Pat. No. 4,393,265 (Bonifaz), U.S. Pat. No. 4,387,263 (Vogt et al.) and European patent application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and ethylene conversion.

General Process Description

In this description, metric units and parts by weight are employed unless otherwise stated. Various reactor configurations may be used, including fluidized bed catalytic reactors, moving bed and fixed bed reactors.

The MTO process may be optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock. Suitable equipment and operating conditions are described in U.S. Pat. application Ser. No. 687,045, filed 28 Dec. 1984, incorporated herein by reference.

The process is depicted in FIG. 1, wherein methanol feed is fed to the oxygenate conversion system in the primary stage and the primary stage effluent is separated in a primary fractionation system to recover heavy liquid, by-product water, ethene-rich light gas and $C_3^+$ hydrocarbons, rich in $C_3$–$C_4$ olefins. The major amount of $C_3$–$C_4$ olefins is fed to the oligomerization reactor system for upgrading to heavier hydrocarbons, especially $C_{10}^+$ distillate range aliphatics and $C_5$–$C_6$ gasoline which may be produced, fractionated and employed as disclosed in U.S. Pat. No. 4,497,968 (Owen et al), incorporated herein.

The $C_3$–$C_4$ hydrocarbon stream from the secondary oligomerization fractionation system contains unconverted propene, butylenes and isobutane; however, the relative amounts of these components are not in stoichiometric balance for alkylation. Accordingly, a slipstream of $C_3$–$C_4$ hydrocarbons, rich in olefins, is taken from the primary fractionation system, and bypasses the oligomerization reactor system. Thus, the alkylation reactor system receives sufficient propene and butylenes to alkylate fresh isoparaffin (e.g., i-$C_4$) derived from the oligomerization reactor system. Excess isoparaffin reactant recovered from the alkylation system is accumulated in a surge drum or similar vessel equipped with liquid level control means LC for detecting level of accumulated isoparaffin and generation of a signal representative of the liquid level for recycle flow control and reactant feed control.

Figure 2:
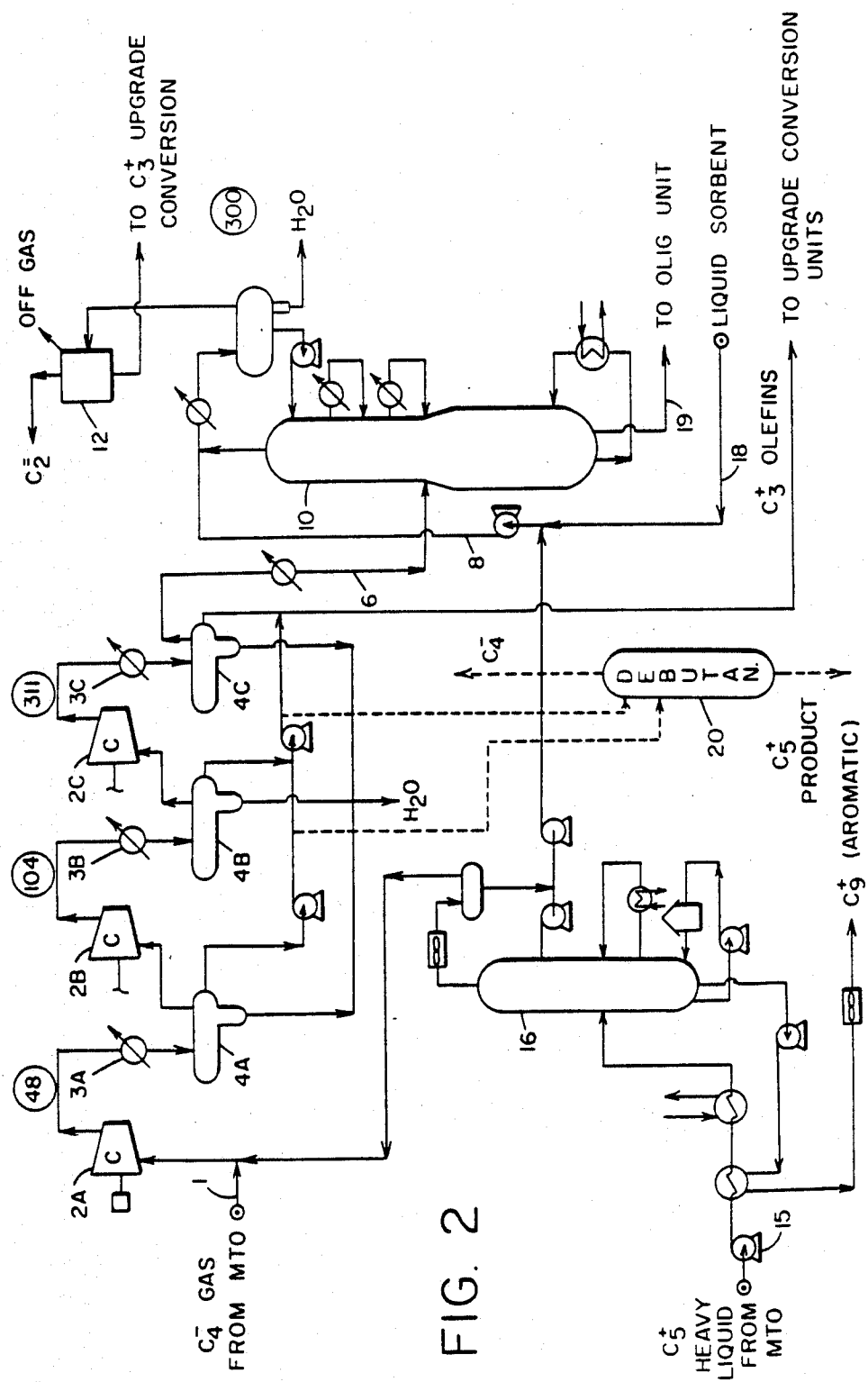
FIG. 2 is a schematic representation of a preferred inter-stage separation system.

In a preferred embodiment depicted in FIG. 2, the primary stage effluent is prefractionated before being sent to olefin upgrading units. Referring to the process diagram of FIG. 2, a gaseous feedstream 1 from an MTO reactor is compressed adiabatically in a series of compressors 3A, B, C and passed through corresponding coolers 3A, B, C and phase separators 4A, B, C to recover by-product water and condensed hydrocarbons containing various amounts of $C_3$–$C_5$ aliphatics. An ethene-rich stream 6 is contacted with a liquid sorbent stream 8 in a countercurrent sorption tower 10. Ethene-rich overhead vapor from tower 10 is further purified in cryogenic separation unit 12 to remove lighter gas and $C_3^+$ components. The purified ethene may be recovered or recycled to the primary stage MTO reactor for further conversion. The $C_3^+$ stream from unit 12 is rich in propene and $C_4$ aliphatics, which may be upgraded by alkylation, by passing the oligomerization reactor.

Heavy liquid separated from the MTO process primary effluent is pressurized by pump 15 and fractionated in tower 16 to recover a $C_9^+$ aromatic-rich stream. The condensed overhead, rich in $C_5^+$ aliphatic and aromatic components is combined with other liquid sorbent (e.g., olefinic gasoline) from line 18 and fed via line 8 to absorber unit 10. $C_3^+$ components sorbed from the feed are removed from column 10 as olefinic sorbate 19, which is a suitable feed to the oligomerization reactor for upgrading to olefinic distillate and gasoline.

As shown by dashed line, an optional debutanizer tower 20 may be employed to recover $C_5^+$ components condensed from the compressor section. The $C_4^-$ overhead from tower 20 may be fed to either the oligomerization or alkylation reactor systems for upgrading.

Figure 3:
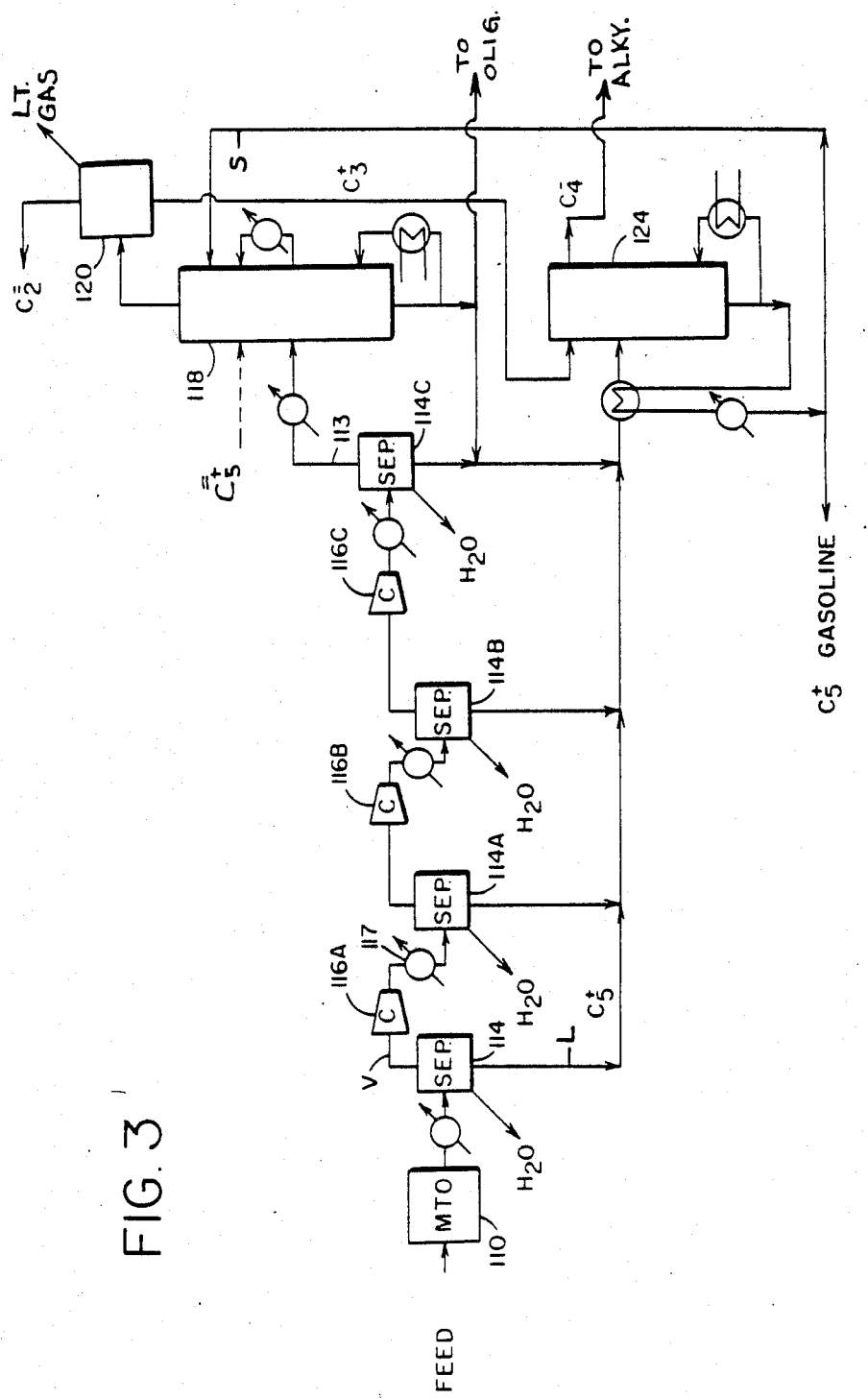
FIG. 3 is an alternative process flow sheet.

In the embodiment of FIG. 3, oxygenate feedstock is converted in MTO unit 110, cooled and passed to separator 114 to provide a $C_5^+$ heavy liquid stream L. The light hydrocarbon vapor stream V separated from the primary stage effluent is compressed in a plurality of compression stages to condense liquid olefinic hydrocarbons. The liquid stream L is combined with a $C_3^+$-rich condensed liquid from succeeding separators. The primary vapor stream is adiabatically compressed by compressor 116A, cooled by exchanger 117 and passed to a succeeding separator 114A, at which point the preceeding phase separation technique is repeated. Likewise other compressors 116B, C and separators 114B and 114C operate to provide an ethene-rich stream, which is passed via line 119 to sorption fractionation unit 118 and optional cryogenic unit 120. Ethene-rich vapor withdrawn from the separator 114C may be processed to increase ethene purity to at least 40% in sorption unit 118. This can be achieved by selectively absorbing $C_3^+$ components in a $C_5^+$ liquid hydrocarbon sorbent stream comprising aliphatic and aromatic hydrocarbons generated in the MTO unit. Advantageously, the MTO effluent is received at about atmospheric pressure (e.g., 100-150 kPa) and compressed in plural stages to a pressure of about 1500-3000 kPa and separated in the final vessel 114C at about ambient temperature (20°-80° C.). Olefinic liquids rich in $C_3^+$ aliphatics may be recovered from the final compressor stage and passed with $C_5^+$ in the liquid hydrocarbon stream L to fractionation tower 124 where $C_5^+$ gasoline sorbent 5 and product are recovered. Olefinic gasoline ($C_5$-$C_9$) may be optionally recycled from the oligomerization stage as additional sorbent if required. A major portion of $C_3$-$C_4$ olefins may be sent to oligomerization directly from absorber 118. A suitable selective sorption unit is disclosed in U.S. Pat. No. 4,450,311 (Wright et al), incorporated herein by reference.

The alkylation process employed herein is a well known industrial technique for reacting alkenes with tertiary alkanes (isoparaffins), such as isobutane, isopentane, isohexane, etc. The resulting product is a $C_7^+$ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21-41 MPa (3000-6000 psi). Under these conditions, both normal and isoparaffins can be brought into reaction by a free-radical mechanism. Thermal alkylation is not known to be practiced commercially.

The catalytic alkylation of paraffins involves the addition of an isoparaffin containing a tertiary hydrogen to an olefin. The process is used in the petroleum industry to prepare highly branched paraffins mainly in the $C_7$ to $C_9$ range, that are high-quality fuels. The overall process is complex, requiring control of operating conditions and of catalyst. The process conditions and the product composition depend on the particular hydrocarbons involved.

The preferred processes are those brought about by the conventional protonic and Lewis catalysts. Propene can be brought into reaction with an isoparaffin in the presence of either concentrated sulfuric acid or hydrogen fluoride. The heptanes produced by alkylation of isobutane with propene are mainly 2,3- and 2,4-dimethylpentane. Propene is alkylated preferably as a component of a $C_3$-$C_4$ fraction. HF catalysts for alkylation of isobutane with 1- and 2-butenes give both dimethylhexanes and trimethylpentanes. The product obtained from alkylation of isobutane with isobutylene at low temperature (e.g., −25° C.) with hydrogen fluoride is 2,2,4-trimethylpentane.

During use the acid catalysts may become diluted with by-product hydrocarbons and as a result decrease in activity. Sulfuric acid concentrations are maintained at about 90%. Hydrogen fluoride concentrations of 80-90% are common, although the optimum concentration depends on the reaction temperature and reactor geometry. Operation below these acid concentrations generally causes incomplete conversion or polymerization. With sulfuric acid, the product quality is improved when temperatures are reduced to the range of 0-10° C. Cooling requirements are obtained by low temperature flashing of unreacted isobutane. With hydrogen fluoride, the reaction process is less sensitive to temperature, and temperatures of 0-40° C. can be used. Some form of heat removal is essential because the heat of reaction is approximately $14 \times 10^5$ J/kg (600 Btu/lb) of butenes converted. Typically the elevated pressure for alkylation by these acid catalysts is about 1500 to 3000 kPa (200-300 psig).

In order to prevent polymerization of the olefin as charged, an excess of isobutane is present in the reaction zone. Isobutane-to-olefin molar ratios of 6:1 to 14:1 are common, more effective suppression of side reactions being produced by the higher ratios.

The typical alkylation reaction employs a two-phase system with a low solubility of the isobutane in the catalyst phase. In order to ensure intimate contact of reactants and catalyst, efficient mixing is provided. This is important with sulfuric acid because of the low solubility of isobutane in the catalyst phase. In addition, the higher viscosity of the sulfuric acid requires a greater mixing energy to assure good contact. The solubility of the hydrocarbon reactants in the catalyst phase is increased by the presence of the unsaturated organic diluent held by the acid catalyst. This organic diluent also has been considered a source of carbonium ions that promote the alkylation reaction.

For the hydrofluoric acid system, reactive i-$C_4H_8$ readily alkylates to give an excellent product. The alkylation of pure 1-$C_4H_8$ by itself proceeds with considerable isomerization of the 1-$C_4H_8$ to 2-$C_4H_8$ followed by alkylation to give a highly branched product. The presence of i-$C_4H_8$ accelerates the alkylation reaction and allows less time for olefin isomerization. Consequently the reaction produces an alkylate with a lowered antiknock value. For the sulfuric acid system, i-$C_4H_8$ tends to oligomerize and causes other side reaction products of inferior quality; but the isomerization of 1-$C_4H_8$ to 2-$C_4H_8$ proceeds more completely, thereby favoring formation of superior products. Thus for mixed olefin feeds such as described above, the two factors with both catalyst systems counteract each other to provide products of similar antiknock properties.

The olefin-producing MTO process may simultaneously generate isobutane, but the amount may be insufficient to alkylate the coproduced olefins. A suitable outside source of isobutane is natural gas or a by-product of methanol-to-gasoline (MTG) processes.

Suitable alkylation processes are described in U.S. Pat. Nos. 3,879,489 (Yurchak et al), 4,115,471 (Kesler), 4,377,721 (Chester) and in the Kirk-Othmer Encyclopedia of Chemical Technology, Vol. 2, pp. 50-58 (3rd Ed., 1978) John Wiley & Sons, incorporated herein by reference.

The combined processes are an effective means for converting oxygenated organic compounds, such as methanol, DME, lower aliphatic ketones, aldehydes, esters, etc, to valuable hydrocarbon products. Thermal integration is achieved by employing heat exchangers between various process streams, towers, absorbers, etc.

Process Control

The following description of preferred control techniques is intended to be implemented by state-of-the-art devices, including a dedicated digital process computer or the like. The protocol for maintaining the process conditions at the desired optimum during plant startup, steady state operation, reactor changeover and shutdown should be carefully delineated. A typical protocol provides the following function: select product quality and capacity; input reactor conditions; feed and recycle rates; establish unit operation limits; sequence reactors and control regeneration loop; monitor process upset and reset control functions. Product streams are controlled to obtain the desired hydrocarbon products; especially for acceptable gasoline and distillate range aliphatics. Various process upsets may be accommodated, such as chnages in feedstock composition. Greater exothermic heat release can be realized by increased lower alkenes in the feedstreams or by increased catalyst activity due to end-of-cycle reactor changeover.

A distributed control system, such as Honeywell TDC-2000 or Foxboro Spectrum, is a preferred control system module; however, equipment selection and operation mode may vary within the inventive concept. Unit operation and fluid handling controls for a typical oligomerization process are disclosed in U.S. Pat. No. 4,554,788 (Daviduk, et al.), including protocol for a digital process computer.

Figure 4:
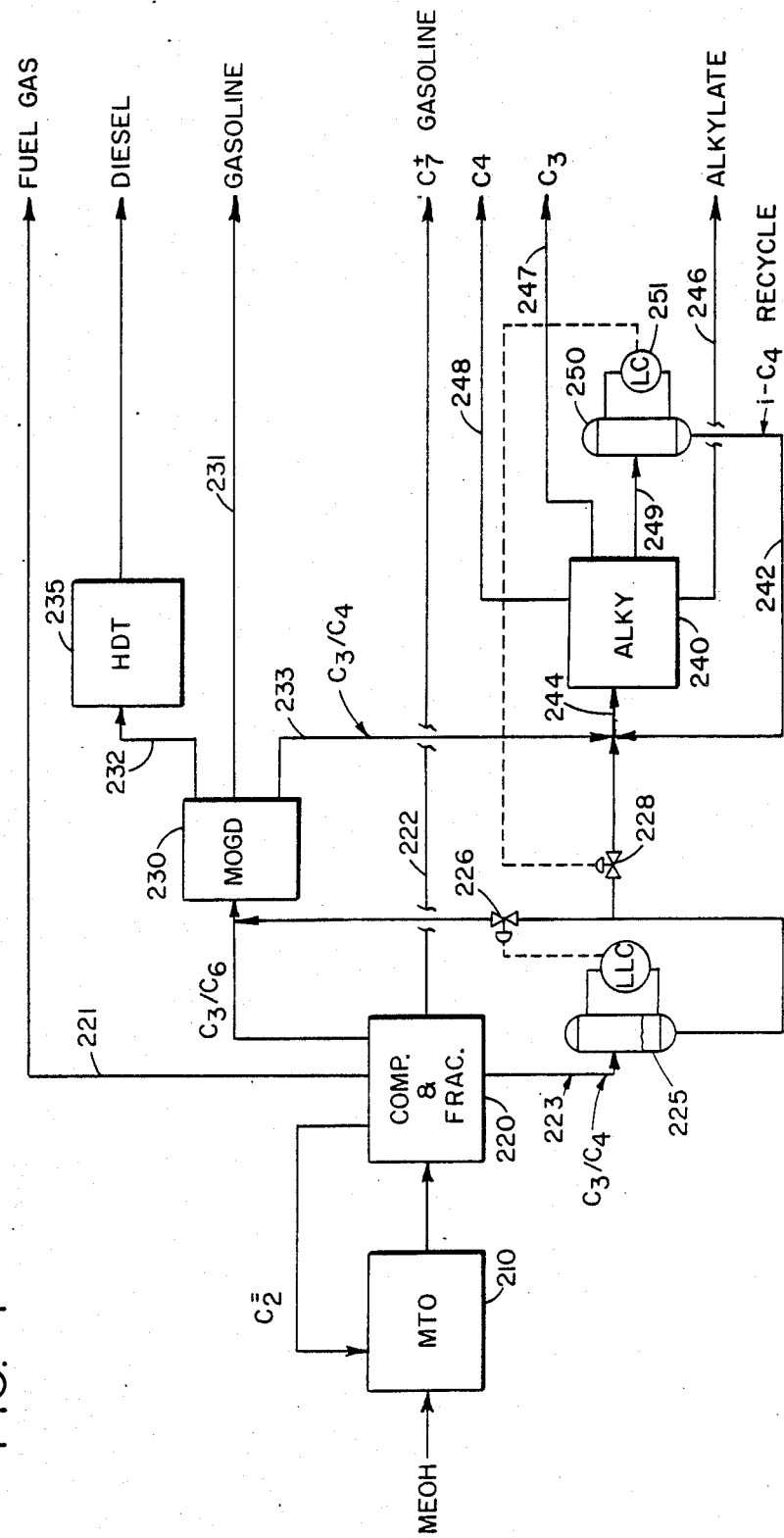
FIG. 4 is a combined process flow sheet and control diagram showing process integration.

The process flowsheet depicted in FIG. 4 shows integration of the unit operations wherein feedstock methanol (MeOH) is converted in MTO primary reactor unit 210 and primary reactor effluent is separated in compression and fractionation section 220, to provide a fuel gas by-product stream 221, $C_7+$ gasoline product stream 222, a $C_3-C_4$ olefin stream 223 and an olefinic feed to MOGD oligomerization unit 230, rich in $C_3-C_6$ olefins.

The MOGD reactor effluent is fractionated to provide additional ($C_5-C_9$) gasoline 231, a $C_{10}+$ distillate stream 232 for treatment in a hydrotreating unit to make diesel grade hydrocarbons, and a $C_3-C_4$ aliphatic stream 233 for feeding to the alkylation unit 240.

A surge drum 225 is provided for receiving the $C_3-C_4$ MTO stream 223. Fluid handling valve means 226 is operatively connected between surge drum 225 and reactor 230 for feeding a predetermined amount of the olefinic feedstream. Valved conduit means 228 is provided for withdrawing a $C_3-C_4$ liquid stream for alkylation.

Control means LLC is provided for detecting liquid level of $C_3-C_4$ olefinic hydrocarbons in surge drum 225 and generating a signal representative of the liquid level. The control means is responsive to the level signal and operatively connected with valve means 226, whereby $C_3-C_4$ stream flow to reactor 230 is increased with increased surge drum liquid level above a predetermined level.

Reactant feed to the alkylation unit 240 from conduit means 228, 233 and recycle 242 is combined in feed conduit 244. The alkylation reaction effluent is fractionated to provide a $C_6+$ alkyate product stream 246, a $C_3$ light product stream 247, a $C_4$ product stream 248 comprising n-butane, and an isoparaffin recycle stream 249 which passes excess isobutane-rich recycle to surge drum 250 for accumulation. Increased $i-C_4$ liquid level in drum vessel 250 is sensed by level control means 251, which signals operation of valve 228 to increase flow of $C_3-C_4$ olefins in response to increased isoparaffin level. Thus, the lower olefin feed to the MOGD oligomerization and alkylation units is balanced according to demand and reaction conditions.

Figure 5:
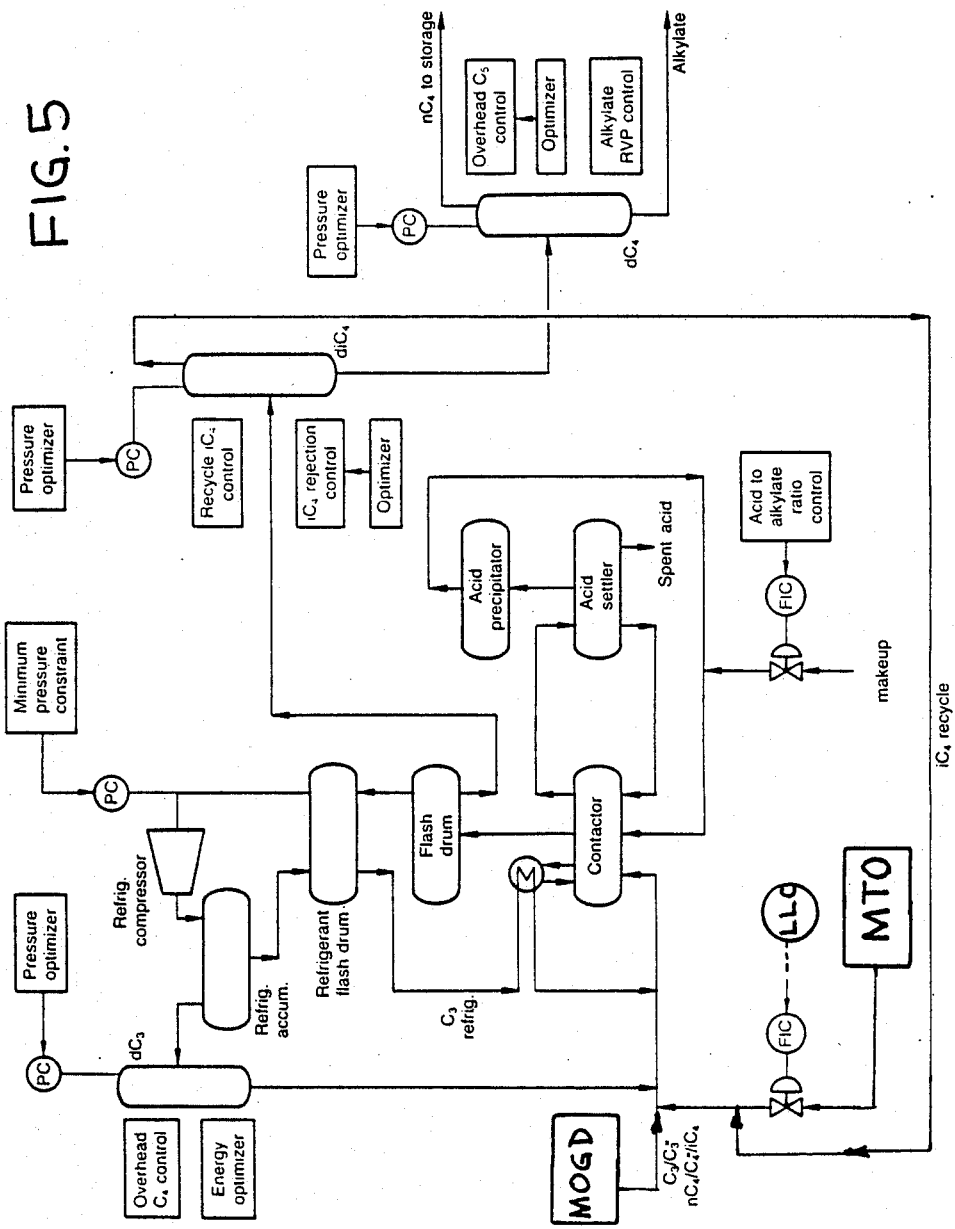
FIG. 5 is a control diagram for a preferred alkylation subsystem.

Control systems for either HF or sulfuric acid and other process sections can be included in the present design, with significant economic benefits derived. State-of-the-art control systems are described in *Hydrocarbon Processing*, Feb. 1986, pp. 53–60. FIG. 5 depicts a modified Setpoint alkylation control system, employing conventional symbols in the instrumentation and control schematic diagram. This control package uses advanced regulatory, feedforward, and constraint controls for optimization. The control functions may be designed in a modular fashion, such that each can be selectively turned on and off without effecting others. Reaction section control functions for the alkyation reactors and acid system are designed to stabilize unit operation and enforce limits to maximize efficiency. The functions include isobutane concentration control, acid to hydrocarbon ratio control and acid strength control. Constraint control functions ensure smooth process response to changes in olefins feed rate while enforcing key process limits. Recycle optimization can be determined for the recycle isobutane stream flow and composition, evaluating trade-offs between energy, acid consumption and alkylate octane.

Various modifications can be made to the system, especially in the choice of equipment and non-critical processing steps. While the invention has been described by specific examples, there is no intent to limit the inventive concept as set forth in the following claims.

I claim:

1. A continuous catalytic process for converting olefinic feedstock comprising ethylene and $C_3+$ olefins to heavier liquid hydrocarbon product comprising the steps of:

prefractionating the olefinic feedstock to obtain a gaseous stream rich in ethylene and a first liquid olefinic stream comprising $C_3-C_4$ olefin;

passing the $C_3-C_4$ liquid olefinic stream to a first accumulator vessel;

contacting a major stream portion of the $C_3-C_4$ olefins from the accumulator vessel with shape selective medium pore zeolite oligomerization catalyst in a distillate mode catalytic reactor zone at elevated temperature and pressure to provide a heavier hydrocarbon effluent stream comprising distillate, gasoline and lighter hydrocarbons;

fractionating the effluent stream to recover distillate, gasoline and a second $C_3-C_4$ hydrocarbon stream containing isobutane;

further reacting a stoichiometric excess of isobutane from the second $C_3-C_4$ hydrocarbon stream with a minor stream of $C_3-C_4$ olefin from the first accumulator vessel in an alkylation reactor zone in the presence of acid alkylation catalyst to produce an effluent stream containing $C_7+$ alkylate;

fractionating the alkylate reactor effluent stream to recover $C_7+$ alkylate product, a $C_3$-light hydrocarbon stream, a stream rich in normal butane and a stream rich in unreacted isobutane;

passing unreacted isobutane to a second accumulator vessel;

recycling isobutane to the alkylation reactor zone at a predetermined rate;

sensing $C_3$-$C_4$ liquid level in the first accumulator vessel;

generating a first control signal representative of said first liquid level;

adjusting fluid flow control means in response to the first control signal to increase flow rate for the major $C_3$-$C_4$ olefinic liquid stream from the first accumulator to the distillate mode oligomerization reactor zone with increased liquid level in the first accumulator vessel;

sensing isobutane liquid level in the second accumulator vessel;

generating a second control signal representative of said isobutane liquid level; and increasing flow of the minor $C_3$-$C_4$ olefin stream from the first accumulator to the alkylation reaction zone in response to the second control signal indicating increased isobutane liquid level in the second accumulator.

* * * * *